United States Patent [19]

Lee

[11] Patent Number: 4,649,122
[45] Date of Patent: Mar. 10, 1987

[54] MEANS FOR DETERMINING PERCENTAGE OF GLYCOHEMOGLOBIN IN WHOLE BLOOD

[75] Inventor: Jin P. Lee, Troy, Mich.

[73] Assignee: Leeco Diagnostics, Inc., Southfield, Mich.

[21] Appl. No.: 247,658

[22] Filed: Mar. 26, 1981

Related U.S. Application Data

[63] Continuation-in-part of Ser. No. 183,545, Sep. 2, 1980, abandoned.

[51] Int. Cl.$^4$ ............................................. G01N 33/72
[52] U.S. Cl. .......................................... 436/67; 436/66
[58] Field of Search ................. 23/230 B, 901, 913, 23/923; 422/69, 70, 101; 436/67, 66

[56] References Cited

U.S. PATENT DOCUMENTS

| | | | |
|---|---|---|---|
| 3,871,832 | 3/1975 | Leblanc | 422/104 |
| 3,996,162 | 12/1976 | McCall | 422/69 X |
| 4,161,104 | 8/1979 | Wagner et al. | 23/230 B X |
| 4,238,196 | 12/1980 | Acuff et al. | 23/230 B |
| 4,268,270 | 5/1981 | Gabbay et al. | 23/913 X |
| 4,269,605 | 5/1981 | Dean et al. | 23/913 X |

FOREIGN PATENT DOCUMENTS 0101052 8/1980 Japan ........................................ 23/913

OTHER PUBLICATIONS

Henry, "Clinical Chemistry—Principles and Techniques", Harper and Row, 1964, pp. 732–734.

*Primary Examiner*—Arnold Turk
*Attorney, Agent, or Firm*—Krass & Young

[57] ABSTRACT

A method is provided for determining the percentage of glycohemoglobin in patient whole blood. The method comprises subjecting total hemoglobin comprising non-carbohydrate fixed hemoglobin and glycohemoglobin of samples of (1) patient whole blood lysate P and (2) whole blood lysates $K_1$ and $K_2$ of known glycohemoglobin percentages $\%_1$ and $\%_2$, to batchwise selective adsorption on an adsorbent which is specific either for the hemoglobin or for the glycohemoglobin, thereby adsorbing each sample under the same conditions and leaving in solution the corresponding non-adsorbed total hemoglobin fractions $P_f$, $K_{1f}$ and $K_{2f}$. The ratios $R_p$, $R_{k1}$ and $R_{k2}$ of the optical density of the total hemoglobin fractions $P_f$, $K_{1f}$ and $K_{2f}$ to the respective optical density of total hemoglobin aliquot samples of lysates P, $K_1$ and $K_2$ are measured, and the percentage of glycohemoglobin relative to total hemoglobin for each patient blood sample is calculated.

22 Claims, No Drawings

MEANS FOR DETERMINING PERCENTAGE OF GLYCOHEMOGLOBIN IN WHOLE BLOOD

CROSS-REFERENCE TO RELATED APPLICATION

This application is a continuation-in-part of application Ser. No. 183,545 filed Sept. 2, 1980, now abandoned.

TECHNICAL FIELD

This invention broadly relates to a new means for determining the content or percentage of glycohemoglobin in batched samples of whole blood.

BACKGROUND ART

The discovery of electrophoretic or chromatographically fast moving minor hemoglobin components of blood was first accomplished by Schroeder et al, *J. Am. Chem. Soc.*, 80:1628 (1958). Various other investigators verified these findings and identified these fast fractions as carbohydrate-linked modifications of normal adult hemoglobin designated as Hgb $A_1a$, $A_1b$, and $A_1c$; see, for example, Clegg et al, ibid., 81:6065 (1959).

Studies have shown that all three fractions are post-transitional modifications and are formed slowly and continuously throughout the 120-day life span of the erythrocyte.

Structural analysis of Hgb $A_1c$ shows a glucose moiety at the amino terminus of each beta chain of normal adult hemoglobin. The formed red cell is unable to initiate protein synthesis. Hgb $A_1c$ is therefore a post formation product, the biosynthesis of which is achieved by the non-enzymatic production of a Schiff base between the aldehyde of the carbohydrate and the amino terminus. An Amadori rearrangement to a stable ketamine then occurs. Hemoglobins $A_1a$ and $A_1b$ appear also to be adducts of carbohydrate metabolites found in normal human erythrocytes. However, their mode of formation is not yet as clearly understood.

Rahbar, in 1968, first reported the presence of elevated levels of glycosylated hemoglobins (glycohemoglobins) in diabetic patients; Clin. Chim. Acta, 22:296 (1968). It was also later shown that these increased levels did not represent the effects of complications of the disease. Finally, hospitalized diabetics showed a marked reduction in Hgb $A_1c$ as control of the disease was accomplished; see *Lancet*, 2:734 (1977); *N. Eng. J. Med.*, 95:417 (1976).

Hemoglobin $A_1c$ is the most abundant of these glycohemoglobins comprising about 3–6% of total hemoglobin concentration. Unlike the lesser components $A_1a$ and $A_1b$, its concentration is in direct proportion to the average amount of circulating blood glucose. It has also been demonstrated that the levels are highest in the oldest of the population of red cells in both diabetics and normal subjects. The measurement of glycohemoglobins of which Hgb $A_1c$ is the major component, is, therefore, a reflection of the glucose levels of a patient over a long period of time and yields a clear assessment of control status with relation to therapy.

Until the present invention, the measurement of Hgb $A_1c$ was a research oriented procedure requiring both sophisticated equipment and considerable time and expense.

Accordingly, one object of the invention is to provide a new method for determining the content or percentage of glycohemoglobins relative to total circulating hemoglobins in patient whole blood.

Another object of the present invention is to provide a new method for determining the percent of glycohemoglobin as an aid to the diagnosis and monitoring of the diabetic patient.

Other objects, features and advantages of the present invention will become apparent from the subsequent description and appended claims.

SUMMARY AND DETAILED DESCRIPTION

Briefly stated, the present invention concerns a method for determining the percentage of glycohemoglobin in patient whole blood, which comprises simultaneously subjecting total hemoglobin comprising non-carbohydrate fixed hemoglobin and glycohemoglobin of each sample of a batch of aliquot samples of (1) patient whole blood lysate P and (2) whole blood lysates $K_1$ and $K_2$ of known glycohemoglobin percentages $\%_1$ and $\%_2$ to selective adsorption on an adsorbent which is specific for either the hemoglobin or for the glycohemoglobin in mixing slurry form in buffer solution thereby adsorbing each sample under the same conditions and leaving in solution the corresponding non-adsorbed or unbound total hemoglobin fractions $P_f$, $K_{1f}$ and $K_{2f}$, measuring the ratios $R_p$, $R_{k1}$ and $R_{k2}$ of the optical density of aliquot samples of the fractions $P_f$, $K_{1f}$ and $K_{2f}$ to the respective optical density of aliquot samples of total hemoglobin lysates P, $K_1$ and $K_2$, and expressing the percentage of glycohemoglobin relative to total hemoglobin for each patient blood sample by a relationship equivalent to $$\frac{R_p(\%_2 - \%_1)}{R_{k2} - R_{k1}} + \%_2 - \frac{R_{k2}(\%_2 - \%_1)}{R_{k2} - R_{k1}}.$$

The method can be used with a wide variety of materials and with considerable variation in the conditions of operation. The method is applicable broadly to one or more human whole blood lysates of unknown glycohemoglobin content and is particularly useful for large batches of blood lysate samples. As used herein, the term "glycohemoglobin" refers to the fast moving hemoglobin components also known as carbohydrate-fixed or carbohydrate-linked hemoglobin. The hemoglobin component of blood will sometimes be referred to herein as non-carbohydrate fixed hemoglobin. The term "total hemoglobin" as applied to a sample includes both the glycohemoglobin in that sample and other hemoglobin, namely, non-carbohydrate fixed hemoglobin.

The blood lysate starting material can be prepared in any suitable way and does not form a part of the invention. In general, at least 0.2 cc of whole blood is required for the analysis. The blood is conveniently collected directly into a vacuum collection tube containing an anti-coagulant such as EDTA and held, if necessary, in storage up to one week at 2°–8° C. The lysate can be prepared from the whole blood in any suitable way. Preferably an aliquot of sequestrinized, well mixed whole blood is added to 5 volumes of lysing solution containing polyoxyethylene ether and potassium cyanide. The solution is then mixed thoroughly and allowed to incubate at room temperature to provide for complete lysis of the cells. The samples of whole blood lysates $K_1$ and $K_2$ are constituted in the same way as patient lysate P samples except that the former have known glycohemoglobin percentages $\%_1$ and $\%_2$ which may be predetermined by conventional means. In a preferred embodiment, the batch may also include a similar whole blood lysate of known hemoglobin percentage for monitoring batch-to-batch and lab-to-lab reproduceability. The selective adsorption of the lysate samples is done under conditions such that the extent of completion of adsorption in each sample is the same. Usually the adsorption is carried out until substantially complete. The preferred adsorption time is about 25 minutes. The adsorption is carried out at temperatures between about 18°–28° C. As indicated, one uses for the adsorption an adsorbent which is specific either for the hemoglobin or for the glycohemoglobin present in each sample, preferably such that the total of either is adsorbed. Thus, where it is desired as to each sample to adsorb the hemoglobin rather than the glycohemoglobin, one uses a specific adsorbent for hemoglobin such as a cation exchange material or resin. Any of a wide variety of materials are suitable. For a comprehensive review of references and materials concerning adsorption and ion exchange, see Chemical Engineers' Handbook, Section 16, McGraw-Hill, 1973. For adsorption of the hemoglobin (as distinguished from the glycohemoglobin), weakly acidic cation exchange materials are preferred such as carboxylic acrylic or methacrylic homogeneous resin, for example Amberlite ® CG50, Amberlite ® IRC-50 and Bio-Rex ® 70. Also, preferred are equivalent polymer adsorbent materials such as polyacrylamide gel or agarose gel which contain a carboxyl group or to which a carboxyl group can be attached to function in the manner of a cation exchanger. Further, where it is desired as to each sample to adsorb the glycohemoglobin rather than the hemoglobin, one uses a specific adsorbent for glycohemoglobin such as an anion exchange material particularly weakly basic material having an organic or resin matrix with amine and quaternary ammonium groups such as aminopolystyrene, aminoethyl and diethylaminoethyl celluloses and the like, or other material having specific binding sites for glycohemoglobin such as carbohydrate-specific supports, e.g., alumina gel, calcium phosphate gel, magnesium carbonate, magnesium silicate, and silica gel, or carbohydrate binding protein conjugated or linked to a solid support or matrix, e.g., glass-lectin, Sepharose ®-lectin, Sephadex ®-lectin, and polyacrylamide gel-lectin. For a discussion of sorbents suitable for diagnostic assay procedures and which are useful as adsorbents for the present invention, see Tietz, Clinical Chemistry, page 157 et seq., W. B. Saunders Co., Phila., 1976; also Lehninger, Biochemistry, 2nd Ed., page 167 et seq., Worth Publishers, Inc., New York, 1975; Peters et al., Chemical Separations and Measurements, page 580 et seq., W. B. Saunders Co., 1974.

For a comprehensive description of suitable solid adsorbent support materials available commercially, see ACKERS, Analytical Gel Chromatography of Proteins, Advances in Protein Chemistry, 24, page 343 et. seq., Academic Press, New York, 1970. For a description of lectin materials and lectin conjugates, see Plant Physiology 64(1), pages 104–107, 1979.

The adsorbent employed is maintained in mixing slurry form in buffer solution. The slurry can be provided according to the invention in any suitable way. For example, it can be supplied by having the adsorbent present in ready-to-use slurry form in aqueous buffer or as a dry slurriable tablet which can be separate from the buffer and subsequently added to the buffer as desired. The adsorbent and lysate sample can be slurried or mixed in any suitable way as by holding the same in a sealed container or tube and rotating, inverting, vibrating, shaking, vortexing or rocking the container. A preferred method is by rotating each container end for end preferably synchronously, and in the range from about 10 to about 20 times per minute.

One preferred embodiment of the invention comprises assembling a batch of aliquot samples of (1) patient whole blood lysate P and (2) whole blood lysates $K_1$ and $K_2$ of known glycohemoglobin percentages $\%_1$ and $\%_2$ such that each sample is contained in a separate sealed container with buffer solution and an adsorbent which is specific either for the hemoglobin or for the glycohemoglobin in slurriable relation, and the containers are mounted in a rack adapted to be moved for mixing the samples synchronously, moving the rack to cause each sample to be mixed in the form of a slurry thereby causing each sample to be adsorbed under the same conditions and leaving in solution the corresponding non-adsorbed total hemoglobin fractions $P_f$, $K_{1f}$ and $K_{2f}$, and measuring the ratios $R_p$, $R_{k1}$ and $R_{k2}$ of the optical density of the fractions $P_f$, $K_{1f}$ and $K_{2f}$ to the respective optical density of aliquot samples of total hemoglobin lysates P, $K_1$ and $K_2$. The rack employed in this embodiment may be a test tube rack or similar device suitable for holding the containers. The rack can be put in motion for mixing in any suitable way. One preferred means for this purpose is a power rotator or tube rack rotator.

The optical density of the aliquot sample can be determined by conventional means. This may be done, for example, by isolating the liquid phase by settling, filtration or centrifugation and by constituting the resulting particulate-free aliquot with cyanide-tris buffer mixture and reading the absorbance of the resultant product spectrophotometrically. Preferably, the samples of the total hemoglobin fractions are centrifuged using a centrifuge preferably rated at 1000×g or more, and the supernatant liquids used for the determination of optical density. Preferably, the optical density of the total hemoglobin fractions is read at a wave-length of 415 nanometers and for total hemoglobin at 540 nanometers.

The invention is illustrated by the following examples.

EXAMPLE 1

Hemoglobin Binding

Materials and Requests

Hemolysis Reagent-one bottle (30 cc) containing an aqueous solution of polyoxyethylene ether (1.2% w/v, Triton ® X-100) and potassium cyanide (0.33% w/v).

Developing Reagent-one bottle (400 cc) containing an aqueous solution of tris-hydroxymethylaminomethane HCl (0.6% w/v) buffer pH 9.5, 0.06% w/v of potassium cyanide and (0.1%) sodium azide as a preservative.

Resin Tubes-12×75 mm polypropylene containing 2.0 cc each of ca. 0.3 g. of cation exchange resin (Amberlite ® IRC-50) slurry in water buffered with tris-hydroxymethylaminomethane pH 6.8.

Reference Standards vials $K_1$ and $K_2$ (1.0 cc each) containing a human whole blood lysate of known glycohemoglobin concentration. Store at 2°–8° C.

Glycohemoglobin Controls-vials (1.0 cc each) containing human whole blood lysate.

12×75 or 13×100 mm tubes
13×100 mm glass cuvette
Test tube rack
Precision 0.10 and 0.50 cc semi-automatic pipettes
Precision semi-automatic dispenser or serologic pipettes for 1.0, 2.0 and 6.0 cc
Test Tube or tube rack rotator capable of causing complete inversion of the tubes (Rotator available from Leeco Diagnostics, Inc., Southfield, Mich., Cat. ROTO1)
Centrifuge capable of obtaining 1000×g.
Spectrophotometer capable of measurement at 415 and 540 nm. (STASAR II, Gilford Co.)

Patient Samples $P_1$, $P_2$ and $P_3$: a minimum of 0.2 cc of whole blood is used for the analysis. Each sample is collected directly into a vacuum collection tube, containing EDTA as an anti-coagulant.

Storage: patient samples may be stored up to one week after collection, at 2°–8° C. Samples should be stored as whole blood and not as hemolysates or packed red cells.

Assay

A. Preparation of Reference Standards and Controls.
  1. Mix one volume of Reference Standard Sample or Control with one volume of Hemolysis Reagent.
  2. Shake and let stand for a few minutes with occasional shaking to assure complete lysis.

B. Preparation of Patient Sample
  1. Label one 12×75 or 13×100 mm hemolysis tube for each patient.
  2. Add 0.1 cc of well mixed whole blood for each patient to the appropriately labeled tube.
  3. Add 0.5 cc of Hemolysis Reagent to all tubes and allow to stand for at least 5 minutes with occasional shaking to assure complete lysis.

GlycoHemoglobin Fraction Assay
  1. Label and uncap one Resin Tube for each sample, Reference Standard and Control. Carefully pipette 1.0 cc of the appropriate hemolyzed sample, Reference or Control onto the top of the buffer solution of each tube.
  2. Replace the cap; rotate all tubes with complete inversion at approximately 14 rpm for 25 minutes.
  3. Centrifuge all tubes at a minimum of 1000×g for 2 minutes.
  4. Label 13×100 mm glass cuvettes for each patient, reference and control and volumetrically transfer 0.5 cc of the clear supernatant liquid from the resin tubes to the appropriately labeled cuvette.
  5. Add 2.0 cc of Developing Reagent to all cuvettes. Mix by inversion and allow to stand for 1 minute.
  6. Determine the absorbance of each cuvette at 415 nm against a distilled water blank.

Total Hemoglobin Fraction Assay
  1. Label one 13×100 mm cuvette for each patient, reference and control.
  2. Pipette 0.10 cc of the appropriate hemolyzed sample (patient, Reference and Control) prepared previously to each cuvette.
  3. Add 6.0 cc of Developing Reagent to all cuvettes. Mix by inversion and allow to stand for 1 minute.
  4. Obtain the absorbance of each sample at 540 nm against a distilled water blank.

Procedural Notes
  1. Total hemoglobin determinations may be conveniently performed during the rotation of the resin tubes.
  2. Alternatively, the total hemoglobin fraction may be performed by using 0.01 cc of lysate in step 2 of Total Hemoglobin Assay and reading at 415 nm.
  3. Care must be exercised while transferring the resin tube supernate to avoid disturbing the resin. Results may be invalidated if resin particles are present in the final reaction mixture.
  4. Test tubes may be substituted for cuvettes in either the total or Glycohemoglobin procedures and transferred to cuvettes for final readings.
  5. For spectrophotometers equipped with diluting and aspirating apparatus, the final dilution of the lysate and glycohemoglobin supernate may be semi-automated. Care must be exercised to treat standards and controls identically to patient samples to maintain the validity of the calculation.
  6. The stoppers on reconstituted Reference Standards and Controls should be replaced immediately upon use and the vials placed back under refrigeration (2°–8° C).
  7. The end point solutions are stable up to 25 hours at room temperature.

Calculation of Results

The slope are intercept values in these calculations are ascertained from a plot of the ratio of the glycohemoglobin to total hemoglobin versus the concentration for the standards supplied.

Step 1: Determine the Ratio (R) in percent due to the glycohemoglobin for each patient, reference and control.

$$R = \frac{\text{O.D. GlyHgb}}{\text{O.D. Total}}$$

Step 2: Find Slope for each batch as follows:

$$\text{Slope} = \frac{\%_2 - \%_1}{R_{k2} - R_{k1}}$$

Step 3: Find Intercept for each batch as follows:

Intercept = $\%_2 - (R_{k2} \times \text{Slope})$

Step 4: Determine the % glycohemoglobin for each patient and control as follows:

%Gly Hgb = (R Patient or Control) × Slope + Intercept

Patient Data

| Patient I.D. | O.D. of GlyHgb Fraction | O.D. of Total Hgb |
|---|---|---|
| STD $K_1$ | .233 | .327 |
| STD $K_2$ | .353 | .335 |
| Patient 1 | .220 | .326 |
| Patient 2 | .382 | .414 |
| Patient 3 | .267 | .343 |

| R (%) | Glycohemoglobin (%) |
|---|---|
| 71.3 | 6.9 (% 1) |
| 105.4 | 15.0 (% 2) |
| 67.5 | 6.0 |
| 92.3 | 11.9 |
| 77.8 | 8.5 |

$$\text{Slope} = \frac{15.0 - 619}{105.4 - 71.3} = 0.238$$

Intercept = 15.0 − (105.4 × 0.238) = −10.04

Patient 1 = (67.5 × 0.238) − 10.04 = 6.0% Clyco Hgb

Patient 2=(92.2×0.238)−10.04=11.9% Glyco Hgb
Patient 3=(77.7×0.238)−10.04=8.5% Glyco Hgb The same procedure can be suitably carried out using an equivalent or comparable quantity of different cation exchanger (in place of IRC-50) such as the proprietary exchangers Bio-Rex®-70, Amberlite® CG50, and Duolite CC-3, or mixtures thereof, and other similar selective adsorbent materials for hemoglobin.

EXAMPLE 2

Glycohemoglobin Binding

The procedure of Example 1 using a hemoglobin adsorbent is followed except that the active agent used in the "Resin Tubes" is a derivatized cellulose adsorbent, diethylaminoethyl (DEAE) cellulose (in the same quantity), instead of a cation exchanger.

Calculation of results and typical patient data are as follows:

Calculation of Results

The slope and intercept values are ascertained from a plot of the ratio of the unbound fraction (or total hemoglobin fraction) to total hemoglobin versus the concentration for the standards supplied.

Step 1: Determine the Ratio (R) in percent due to the unbound fraction (hemoglobin) for each patient, reference and control.

$$R = \frac{\text{O.D. Unbound Fraction}}{\text{O.D. Total}}$$

Step 2: Find Slope for each batch as follows:

$$\text{Slope} = \frac{\%_2 - \%_1}{R_{k2} - R_{k1}}$$

Step 3: Find Intercept for each batch as follows:

Intercept = $\%_2 - (R_{k2} \times \text{Slope})$

Step 4: Determine the % glycohemoglobin for each patient and control as follows:

%Gly Hgb = (R Patient or Control) × Slope + Intercept

Patient Data

| Patient I.D. | O.D. of Unbound Fraction | O.D. of Total Hgb |
|---|---|---|
| STD K$_1$ | .593 | .340 |
| STD K$_2$ | .567 | .383 |
| Patient 1 | .737 | .338 |
| Patient 2 | .638 | .386 |
| Patient 3 | .466 | .390 |
| R (%) | Glycohemoglobin (%) | |
| 174 | 7.1 (% 1) | |
| 148 | 10.3 (% 2) | |
| 218 | 1.7 | |
| 165 | 8.2 | |
| 119 | 13.9 | |

Calculation $$\text{Slope} = \frac{10.3 - 7.1}{148 - 174} = -0.123$$

Intercept = 10.3 − (−0.123 × 148) = 28.5

Any of various glycohemoglobin adsorbents or binders can be used in the procedure of Example 2 in place of the DEAE-cellulose, with the same result. Among these adsorbent grade materials, for example, are alumina gel, calcium phosphate gel, magnesium carbonate, magnesium silicate, silica gel (silicic acid), activated carbon, DEAE-Sephadex®, aminopolystyrene (Amberlite® IRA-45), ECTEOLA-cellulose, Sepharose-lectin (Concanavalin A) and other similar conjugated carbohydrate binding lectins.

While the invention is described in detail in the foregoing specification, it will be realized by those skilled in the art that considerable variation can be made in such detail without departing from the spirit and scope of the claims which follow.

I claim:

1. A method for determining the percentage of glycohemoglobin in patient whole blood, which comprises:

simultaneously subjecting total hemoglobin comprising non-carbohydrate fixed hemoglobin and glycohemoglobin of each sample of a batch at a common temperature of aliquot samples of
(1) a plurality of whole blood lysates P and
(2) whole blood lysates K$_1$ and K$_2$ of known glycohemoglobin percentages %$_1$ and %$_2$ to adsorption on an adsorbent which is specific either for the hemoglobin or for the glycohemoglobin in mixing slurry form in buffer solution, each sample being contained in its own sealed container of uniform size and shape and the batch of thus contained samples being synchronously mixed together by common agitation as a batch thereby adsorbing each sample under the same temperature conditions and leaving in solution the corresponding non-adsorbed total hemoglobin fractions P$_f$, K$_{1f}$ and K$_{2f}$,
measuring the ratios R$_p$, R$_{k1}$ and R$_{k2}$ of the optical density of aliquot samples of the fractions P$_f$, K$_{1f}$ and K$_{2f}$ to the respective optical denisty of aliquot samples of total hemoglobin lysates P, K$_1$ and K$_2$, and expressing the percentage of glycohemoglobin relative to total hemoglobin for each patient blood sample by the relationship equivalent to $$\frac{R_p(\%_2 - \%_1)}{R_{k2} - R_{k1}} + \%_2 - \frac{R_{k2}(\%_2 - \%_1)}{R_{k2} - R_{k1}}.$$

2. A method according to claim 1 wherein the adsorbent is specific for the glycohemoglobin.

3. A method according to claim 2 wherein the adsorbent comprises derivatized cellulose.

4. A method according to claim 1 wherein the adsorbent is specific for the hemoglobin.

5. A method according to claim 4 wherein the adsorbent comprises cation exchange material.

6. A method according to claim 1 wherein the patient lysate P comprises a plurality of patient whole blood lysates which are each randomly comparable batchwise to the lysates of known glycohemoglobin percentage in the batch.

7. A method according to claim 4 which is one of a series of batches and each batch comprises a common whole blood lysate of known glycohemoglobin percentage for monitoring batch-to-batch reproduceability.

8. A method according to claim 1 wherein each sample for adsorption is contained in a sealed tube of uniform size and shape and the adsorption is carried out by rotating each tube end for end.

9. A method according to claim 8 wherein the samples are rotated synchronously.

10. A method according to claim 9 wherein each sample is rotated at constant rate in the range from about 10 to about 20 rotations per minute.

11. A method according to claim 10 wherein each sample is rotated about 14 rotations per minute for 25 minutes.

12. A method according to claim 1 wherein the total hemoglobin fractions are centrifuged and aliquots of the total hemoglobin lysates and of the resulting supernatant liquids are analyzed for optical density.

13. A method according to claim 1 wherein the adsorption is carried out until substantially complete.

14. A method according to claim 1 wherein the adsorption temperature is in the range from 18° to 28° C.

15. A method for determining the percentage of glycohemoglobin in patient whole blood comprising hemoglobin and glycohemoglobin, which comprises:

assembling a batch at a common temperature of aliquot samples of
(1) a plurality of whole blood lysates P and
(2) whole blood lysates $K_1$ and $K_2$ of known glycohemoglobin percentages $\%_1$ and $\%_2$ such that each sample is contained in a separate sealed container with buffer solution and an adsorbent which is specific either for the hemoglobin or for glycohemoglobin in slurriable relation, and the containers are mounted in a rack adapted to be moved for mixing the samples synchronously, moving the rack to cause the hemoglobin of each sample to be mixed in the form of a slurry thereby causing each sample to be adsorbed under the same temperature conditions and leaving in solution the corresponding non-adsorbed total hemoglobin fractions $P_f$, $K_{1f}$ and $K_{2f}$, measuring the ratios $R_p$, $R_{k1}$ and $R_{k2}$ of the optical density of the total hemoglobin fractions $P_f$, $K_{1f}$ and $K_{2f}$ to the respective optical denisty of aliquot samples of total hemoglobin lysates P, $K_1$ and $K_2$, and determining the percentage of glycohemoglobin relative to total hemoglobin for each patient blood sample by the relationship equivalent to $$\frac{R_p(\%_2 - \%_1)}{R_{k2} - R_{k1}} + \%_2 - \frac{R_{k2}(\%_2 - \%_1)}{R_{k2} - R_{k1}}.$$

16. A method according to claim 15 wherein the adsorbent is specific for glycohemoglobin.

17. A method according to claim 16 wherein the adsorbent comprises derivatized cellulose.

18. A method according to claim 15 wherein the adsorbent is specific for non-carbonhdrate fixed hemoglobin.

19. A method according to claim 18 wherein the adsorbent comprises cation exchange material.

20. A method according to claim 15 wherein the optical density is measured spectrophotometrically.

21. A method according to claim 15 wherein the optical density of the total hemoglobin fractions is read at a wave-length of 415 nanometers.

22. A method according to claim 15 wherein the optical density for total hemoglobin is read at a wave-length of 540 nanometers.

* * * * *

UNITED STATES PATENT AND TRADEMARK OFFICE
CERTIFICATE OF CORRECTION

PATENT NO. : 4,649,122

DATED : March 10, 1987

INVENTOR(S) : Jin P. Lee

It is certified that error appears in the above-identified patent and that said Letters Patent is hereby corrected as shown below:

Column 8, line 41 "denisty" should be --density--.

Column 10, line 22, "non-carbonhdrate" should be --non-carbohydrate--.

Signed and Sealed this

Twenty-second Day of September, 1987

Attest:

DONALD J. QUIGG

Attesting Officer     Commissioner of Patents and Trademarks